(12) United States Patent
Tilley

(10) Patent No.: US 8,069,853 B2
(45) Date of Patent: Dec. 6, 2011

(54) BREATH RESPONSIVE POWERED AIR-PURIFYING RESPIRATOR

(75) Inventor: Greg A. Tilley, Monkton, MD (US)

(73) Assignee: Immediate Response Technologies, Glen Dale, MD (US)

( * ) Notice: Subject to any disclaimer, the term of this patent is extended or adjusted under 35 U.S.C. 154(b) by 1055 days.

(21) Appl. No.: 11/893,124

(22) Filed: Aug. 14, 2007

(65) Prior Publication Data

US 2008/0196723 A1  Aug. 21, 2008

Related U.S. Application Data

(60) Provisional application No. 60/838,123, filed on Aug. 14, 2006.

(51) Int. Cl.
*A61M 16/00* (2006.01)

(52) U.S. Cl. ......... 128/204.18; 128/204.21; 128/204.22; 128/204.26; 128/205.24; 128/205.25

(58) Field of Classification Search ............. 128/204.18, 128/204.21, 204.22, 204.26, 205.12, 205.25
See application file for complete search history.

(56) References Cited

U.S. PATENT DOCUMENTS

| | | | | |
|---|---|---|---|---|
| 5,111,809 A | * | 5/1992 | Gamble et al. ........... | 128/204.18 |
| 5,148,802 A | * | 9/1992 | Sanders et al. ........... | 128/204.18 |
| 5,551,419 A | * | 9/1996 | Froehlich et al. ........ | 128/204.23 |
| 5,865,173 A | * | 2/1999 | Froehlich ................. | 128/204.23 |
| 6,367,474 B1 | * | 4/2002 | Berthon-Jones et al. | 128/204.23 |
| 6,443,154 B1 | * | 9/2002 | Jalde et al. ............... | 128/205.29 |
| 6,631,716 B1 | * | 10/2003 | Robinson et al. ........ | 128/204.21 |
| 6,705,314 B1 | * | 3/2004 | O'Dea ..................... | 128/204.18 |
| 6,752,151 B2 | * | 6/2004 | Hill .......................... | 128/204.18 |
| 6,932,084 B2 | * | 8/2005 | Estes et al. ............... | 128/204.18 |
| 6,968,842 B1 | * | 11/2005 | Truschel et al. ......... | 128/204.18 |
| 7,152,598 B2 | * | 12/2006 | Morris et al. ............ | 128/204.23 |
| 7,168,429 B2 | * | 1/2007 | Matthews et al. ........ | 128/204.21 |
| 7,481,215 B2 | * | 1/2009 | Rossen et al. ............ | 128/203.12 |
| 2002/0104536 A1 | * | 8/2002 | Richey, II ................ | 128/204.22 |
| 2003/0127096 A1 | * | 7/2003 | McAuliffe et al. ...... | 128/204.18 |
| 2004/0035422 A1 | * | 2/2004 | Truitt et al. .............. | 128/204.18 |
| 2005/0016536 A1 | * | 1/2005 | Rapoport et al. ........ | 128/204.18 |
| 2005/0109341 A1 | * | 5/2005 | Alvey ...................... | 128/205.12 |
| 2005/0268913 A1 | * | 12/2005 | Morris et al. ............ | 128/204.23 |
| 2006/0027234 A1 | * | 2/2006 | Gradon et al. ........... | 128/204.21 |
| 2006/0090759 A1 | * | 5/2006 | Howes et al. ............ | 128/204.21 |

\* cited by examiner

*Primary Examiner* — Justine Yu
*Assistant Examiner* — Clinton T Ostrup
(74) *Attorney, Agent, or Firm* — Duane Morris, LLP

(57) ABSTRACT

A system for regulating the airflow to a closed environment using feedback control for the position of a control valve and blower speed. The system provides a control apparatus that regulates airflow to a closed environment, such as the mask of a breathing apparatus, to ensure sufficient breathing air for a wearer of such mask. In order to provide fast response to a change in condition in the breathable environment, the airflow regulator includes a valve control and a blower control.

5 Claims, 3 Drawing Sheets

BREATH RESPONSIVE POWERED AIR-PURIFYING RESPIRATOR

CROSS REFERENCE TO RELATED APPLICATION

This application is based upon and claims benefit of co-pending U.S. Provisional Patent Application Ser. No. 60/838,123, filed with the U.S. Patent and Trademark Office on Aug. 14, 2006 by the inventor herein, the specification of which is incorporated herein by reference.

BACKGROUND OF THE INVENTION

1. Field of the Invention

This invention is directed to an airflow regulating system and more particularly to an apparatus that is useful in purifying contaminated air for assisting persons to breathe in hostile environments.

2. Background of the Invention

There are, at present breathing systems for assisting the breathing of persons who are subject to contaminated air. There are filter/decontamination systems for use in the form of a canister, in connection with a respirator apparatus that rely on cleaning ambient atmosphere to make it suitable for breathing. Such filter systems may or may not make use of auxiliary power. In powered systems, ambient atmosphere is sucked through a suitable filter/decontamination means, or other purifying means, by a powered fan or the like, such that the contaminated ambient air is rendered breathable. The purified resultant air is fed to a headpiece of some kind, such as a tight fitting facemask. The complete system is known as a Powered Air Purifying Respirator (PAPR). Such breathing assists are used by personnel who are subject to breathing ambient atmosphere that would otherwise be considered to be harmfully contaminated, un-breathable, or dangerous air. Firefighters and others in the emergency response arena may use PAPRs equipped with filter canisters, such as HEPA filters, to provide filtered ambient air to any user who is operating in a hazardous environment.

A dangerous or un-breathable atmosphere is considered to be air containing less than 19.5 volume percent oxygen, or air with the requisite oxygen, but also containing significant proportions of harmful contaminants, e.g. particulate or gaseous. A PAPR system will protect against contaminants so long as the oxygen level in the purified air is above 19.5 volume percent and provided the contaminants are such as can be removed by filtration, e.g. soot and smoke, and/or can be ameliorated by reaction with a suitable purifying material. In practical effect, these systems have been designed to use replaceable filter(s) and air purifying canister(s). However, they are of no value where the ambient atmosphere has an oxygen content that is less than 19.5% by volume. It will be appreciated that, in some situations, (where the oxygen content is at least 19.5%), a wearer may be able to enter an area that has a contaminated atmosphere using only a filter system, provided the filter(s) is capable of meeting the challenge of the contamination, as a result cleaning the atmosphere and enabling the user to breathe and still preserve his health. The filter can be provided with means to eliminate harmful constituents in the wearer's ambient atmosphere. In particular, filter based decontamination systems, that is, those systems that purify an ambient atmosphere that has become contaminated so as to convert it to breathable air, work best when they pass an air supply under positive pressure through a cleaning element (such as a suitable filter). That is, a pump/fan is used to suck the contaminated atmosphere through a filter, and perhaps into contact with a material that ameliorates the contaminant(s), and to then force the purified, e.g. filtered, air under positive pressure into a facemask or other means associated with the breathing of the wearer, such as a mouth grip, hood, or helmet. While a powered air supplying means, such as a battery-operated pump/fan, is probably preferred, it is also known that air-cleaning systems that are not powered by external means can be used. In these unpowered systems, the user's lung power provides the necessary impetus to force contaminated air through the cleaning element and feed it to the user. For simplicity, this means of cleaning ambient atmosphere will be referred to as an Air Purifying Respirator (APR). When the air is forced through the system due to the use of a battery, line current or other powered pump or fan arrangement, the operating system is known as a Powered Air Purifying Respirator (PAPR).

Given the growing demand for PAPR systems, requirements have been identified for providing breath responsive systems that would allow longer filter life, conservation of battery power, and provide air generally on a demand basis so as to better simulate the user's natural breathing pattern. However, while prior efforts have been made to provide breath-responsive systems, shortcomings of prior constructions have prevented their commercial acceptance.

Thus, there remains a need for a breathing assist system that is capable of supplying breathable air to a user, but that does so while maximizing efficiency of the apparatus and that preferably supplies only the amount of air that the user's actual demand for air dictates.

The above and following comments use a fire fighter as illustrative of the type of person who will benefit from using the instant invention. However, this invention is by no means limited in use to fire fighters. Workers in chemical plants and refineries will have substantial need for the benefits available from the instant invented system. Soldiers in the field that are being subjected to chemical or biological attack will benefit greatly from the instant system. It will be apparent to those of ordinary skill in this art that others will similarly be assisted by the instant invention.

SUMMARY OF THE INVENTION

The present invention provides a solution to the above and other problems by enabling a powered air-purifying respirator system for supplying clean, breathable air from ambient surroundings to a respirator hood or facemask.

In a first aspect of the present invention, an airflow regulating system is provided that supplies air to the user by controlling the amount of air supplied in response to a sensed condition within the user's breathable environment. In a particularly preferred embodiment, a pressure transducer that senses the pressure of air within, or the pressure of air delivered to, the user's breathable environment is provided, and in response to the sensed pressure condition, an airflow regulator controls the amount of air supplied to the user's breathable air environment.

In accordance with a particularly preferred embodiment, the system includes a powered blower unit that draws air through one or more filter canisters and directs such filtered air to the user's breathable environment, for example, a tight-fitting mask over at least a portion of the user's face. Within the flow path from the blower to the breathable environment, an airflow regulator is provided to control the amount of air that is delivered to the user's breathable environment at any given time. The airflow regulator is configured to provide fast response (i.e., fast opening and closing of the valve member) in response to changes in a condition within the breathable environment, and preferably changes in the pressure within the breathable environment. In order to provide fast response to a change in condition in the breathable environment, the airflow regulator in accordance with a preferred embodiment includes a valve control that allows forced air from the blower to be directed to the user's breathable environment. In a further preferred embodiment, the airflow regulator includes a motor control that allows automatic changes in the speed of the blower.

In accordance with another aspect of a preferred embodiment of the invention, a blower unit is provided that is configured to direct pressurized air to the airflow regulator, and on to the user's breathable environment. The blower unit preferably comprises a motor driving a centrifugal fan and at least one filter canister to filter air drawn into the blower. Optionally, the blower unit may be provided a purge valve used to divert the flow of air exiting the blower unit from a first port that directs air to the user to a second port that directs the air to the outside environment. Such purge valve may be useful to allow air to constantly be drawn through the filter, and thus keep the filter cool. Moreover, such purge valve assembly may be useful to allow the filters to be cleaned by running clean air through the filters to pull out contaminants, and directing such cleansing air to the outside environment instead of to the user's breathable environment.

In accord with and fulfilling these objects, one aspect of this invention is a breathing assisting apparatus comprising a tight fitting facemask, or other conventional means of bringing respirating air to a person in need thereof, that is adapted to be tightly fitted to a person's face or mouth or nose (or any combination thereof). For ease of understanding, further reference will be made to the use of a facemask. However, this use is illustrative and not limiting. A mouthpiece can also serve the function of bringing the breathable air to the user.

Other and additional objects of this invention will become apparent from a consideration of this entire specification.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION

The invention summarized above and defined by the enumerated claims may be better understood by referring to the following description, which should be read in conjunction with the accompanying drawings. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
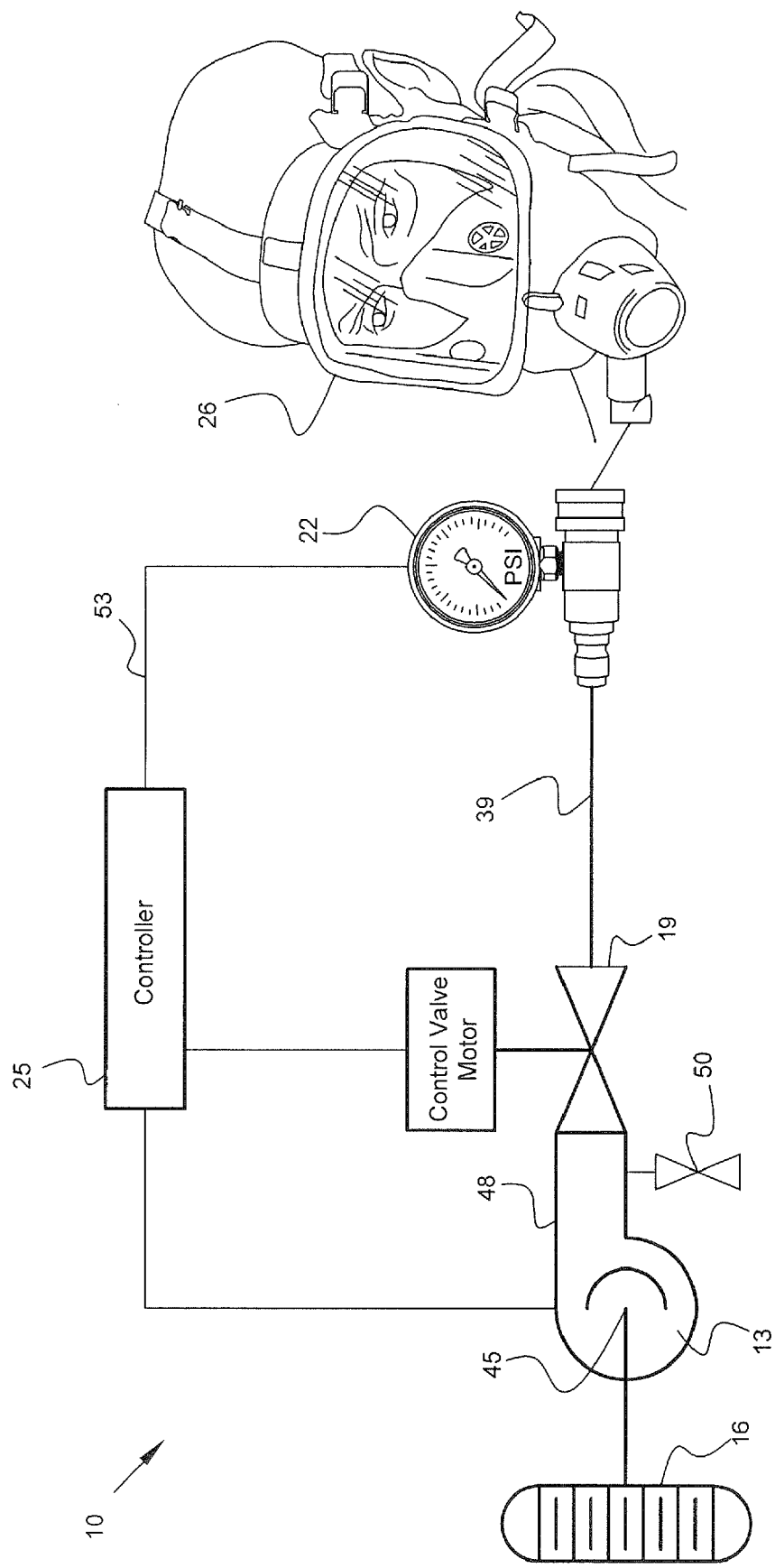
FIG. 1 is a schematic diagram of an air supply system according to a first embodiment of this invention.

In an effort to avoid the above-described disadvantages, a control system for a powered air-purifying respirator unit is provided. As shown in FIG. 1, the system according to a first preferred embodiment is shown generally at 10, and comprises a blower assembly 13, a filter manifold 16, a control valve 19, a pressure sensor 22, and a main circuit controller 25. The system is operatively connected to a facemask 26.

Figure 2:
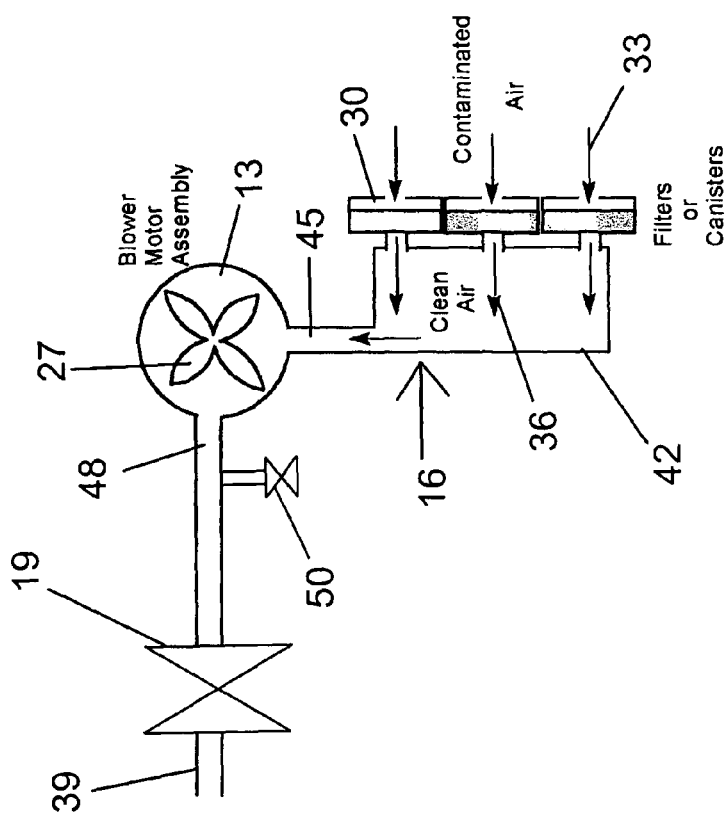
FIG. 2 is a diagram of a cutaway portion of the air supply system of FIG. 1.

Referring to FIGS. 1 and 2, in a preferred embodiment, blower assembly 13 comprises a motor and impeller type fan 27. The blower assembly 13 is operatively connected to the filter manifold 16 that includes a plurality of filter/decontamination elements 30. The impeller fan 27 provides means for moving ambient air 33 through the filter manifold 16 and through the filter/decontamination elements 30. In a preferred embodiment, the impeller fan 27 is rotated by a variable speed, electric motor that is powered by one or more batteries. In a preferred embodiment, the battery is a Lithium polymer rechargeable battery or a Nickel-Cadmium rechargeable battery. Other types of batteries can be used. A charging port for the battery may also be provided. The impeller 27 in the blower assembly 13 is adapted to cause ambient air to be drawn through the filters or canisters (containing suitable decontamination) in the filter manifold 16 where the air is to be cleaned of solid particulate matter, harmful gases, and/or odors to produce cleaned air. The cleaned air 36 is forced into the facemask 26 worn by a user to thereby provide breathable air to the wearer. The facemask 26 is connected to the blower assembly 13 via a hose 39.

Further, in a preferred embodiment, the filter manifold 16 comprises a shell 42 for holding at least one filter/decontamination element 30 of standard construction, selected for the threat/contagion environment in which the unit is intended to be used. Such filter/decontamination element 30 may be configured to filter dust, chemicals, gases, biological agents, etc., as is known in the art. Subject to the class of filter/decontamination elements fitted and the time spent in the contaminated area, the filter/decontamination elements 30 may provide breathable air 36 in a chemically, biologically, or nuclear contaminated environment. The filter manifold 16 is sized and configured to hold a plurality of filter/decontamination elements 30 and may be integrally formed with, embedded in, or otherwise sealingly attached to a plenum 45 at the inlet of the blower assembly 13, such that the only available flow path to the fan impeller 27 is through the filter/decontamination elements 30 in the filter manifold 16. The filter manifold 16 supports at least one, and preferably a plurality of filter/decontamination elements 30. The exit from each filter/decontamination elements 30 is preferably operatively associated with the facemask 26 so that contaminated air 33 drawn into each filter/decontamination element 30 by means of the blower assembly 13 is cleaned and then powered by the impeller 27 into the facemask 26 via the hose 39 and control valve 19. All air passing through any and all specific filter/decontamination element(s) 30 exit into the inlet plenum 45 that is operatively associated with the blower assembly 13, as stated above. In FIG. 2, there are shown three (3) filter/decontamination elements 30 each of which contain filter medium. One or more of the canisters can also contain suitable materials that serve to decontaminate the ambient environmental air by eliminating harmful components that are not filterable. The individual filter/decontamination elements 30 can be used individually or in plural configuration and may be fitted all on one side of the shell 42 or fitted some on one side and some on the other to the desired quantity. As the filter/decontamination element 30 is intended as a disposable unit, the outer shell 42 of filter manifold 16 should be formed of an inexpensive material, such as plastic. The entire filter manifold 16 may simply be disposed of and replaced when it comes time to replace the filter/decontamination elements 30. In another embodiment, individual filter/decontamination elements 30 may be replaced.

Control valve 19 is preferably a motor-operated butterfly valve having a stepper motor to enable positioning of the control valve 19 as directed by the main circuit controller 25. For ease of construction and wearing of the system 10, the control valve 19 should be located close to the blower assembly and may be integrally formed with, embedded in, or otherwise sealingly attached to the outlet 48 of the blower assembly 13.

A purge valve 50 may be provided between the blower assembly outlet 48 and the control valve 19. The purge valve should be a normally closed, manually operated valve that can be used to divert the flow of air exiting the blower assembly 13 directly to the outside environment. Such purge valve 50 may be useful to allow air to constantly be drawn through the filter/decontamination elements 30, and thus keep them cool. Moreover, such purge valve 50 may be useful to allow the filter/decontamination elements 30 to be cleaned by running clean air through them to pull out contaminants, and directing such cleansing air to the outside environment instead of to the user's breathable environment.

The pressure tap 22 is attached to the hose 39 in a position as close to the facemask 26 as possible. A tube 53 connects the pressure tap 22 to a solid-state pressure transducer in the main circuit controller 25. The opposite side of the solid-state pressure transducer is vented to atmosphere. The pressure tap 22 senses pressure in the facemask 26 as an indication of breathing need of the user.

The main circuit controller 25 comprises sensors and drivers to operate the blower assembly 13 and control valve 19. As indicated above, a solid-state pressure transducer for reading facemask pressure is provided. A stepper motor driver is provided for operation of the control valve motor and a brushless motor driver is provided for operation of the blower motor. The main circuit controller 25 also includes two microcontrollers: one for reading facemask pressure and adjusting the position of the control valve 19 and the other for adjusting the speed of the blower assembly 13. In a preferred embodiment, the main circuit controller 25 may also include one or more USB ports, a real-time clock, and memory for data logging.

Figure 3:
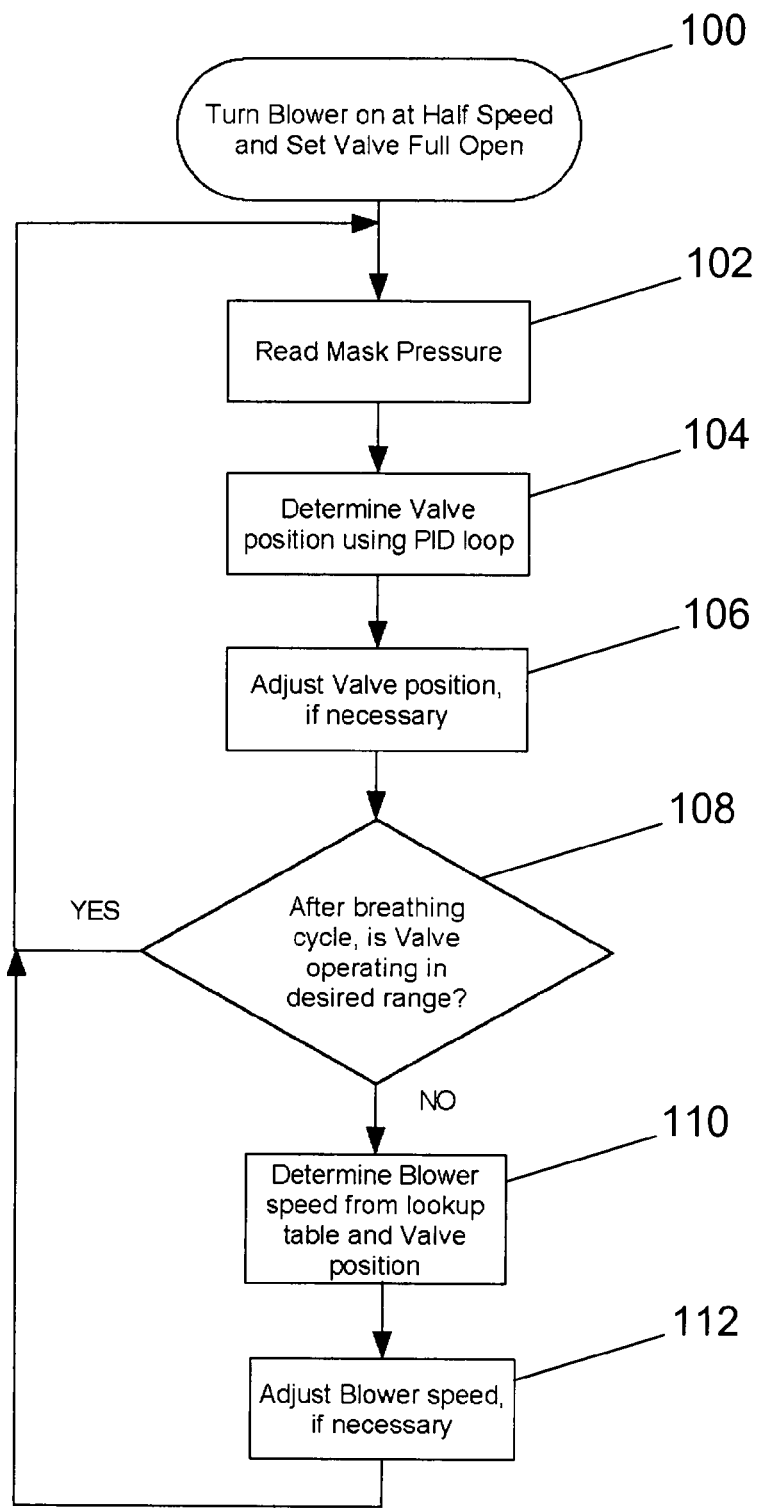
FIG. 3 is a flow chart of a control algorithm according to a first embodiment of the invention.

In a preferred embodiment, the main circuit controller 25 uses a PID controller to operate the control valve 19 and blower motor. The PID controller uses feedback from the valve position and/or blower speed in conjunction with facemask pressure to provide sufficient breathing air to the user. Referring to FIG. 3, a flowchart of the basic operation of the system is shown. Initially, at step 100, the blower assembly 13 is turned on at half speed and the control valve 19 is set to full open. At step 102, the controller reads the facemask pressure. Then, at step 104, the PID controller determines an appropriate position for the control valve 19, based on pressure and the current position of the control valve 19. If necessary, at step 106, the main circuit controller 25 sends a signal to the control valve motor to adjust the position of the control valve. At step 108, the main circuit controller 25 determines if the control valve 19 is operating in a preselected desired range. If so, control of the breathing air pressure to the facemask 26 is maintained by feedback in the PID control loop. If the control valve 19 is not operating in the desired range then, at step 110, an appropriate speed for the blower is determined from a look-up table based on the current position of the control valve 19. If necessary, at step 112, the main circuit controller 25 sends a signal to the blower motor to adjust the speed of the blower. The use of the PID controller and separate control of the valve position and blower speed minimizes movement of the control valve 19 and variation in the speed of the blower.

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

What is claimed is:

1. A breath responsive respirator system, comprising: a facemask; a blower operatively connected to the facemask, the blower being capable of forcing air to the facemask; a filter manifold operatively connected to the blower; a control valve; a pressure sensor operatively connected to a controller which detects a pressure condition within the facemask; the controller operatively connected to the blower and the control valve and the controller controls operation of the blower and the control valve; and, a purge valve integrated with the blower that can be used to divert the flow of air exiting the blower directly to the outside environment.

2. The breath responsive respirator system according to claim 1, wherein the purge valve is manually operated.

3. The breath responsive respirator system according to claim 1, wherein the purge valve is normally closed during operation of the blower.

4. A breath responsive respirator system, comprising: a facemask; a blower operatively connected to the facemask, the blower being capable of forcing air to the facemask; a filter manifold operatively connected to the blower; a control valve; a pressure sensor operatively connected to a controller which detects a pressure condition within the facemask; the controller operatively connected to the blower and the control valve and controls operation of the blower and the control valve wherein the controller processes a signal transmitted by the control valve and transmits a signal to the blower and wherein the controller processes a signal transmitted by the blower and transmits a signal to the control valve; and a purge valve integrated with the blower that can be used to divert the flow of air exiting the blower directly to the outside environment.

5. A breath responsive respirator system, comprising: a facemask; a blower operatively connected to the facemask, the blower being capable of forcing air to the facemask; a filter manifold operatively connected to the blower; a control valve; a pressure sensor operatively connected to a controller which detects a pressure condition within the facemask; the controller operatively connected to the blower and the control valve and controls operation of the blower and control valve; wherein the facemask is adapted to establish and maintain a seal with the face of a user so as to isolate at least the nose and mouth of the user from ambient air, and adapted to maintain the seat under conditions of positive pressure within the facemask; and a purge valve integrated with the blower that can be used to divert the flow of air exiting the blower directly to the outside environment.

* * * * *